(12) United States Patent
Abels et al.

(10) Patent No.: US 10,570,514 B2
(45) Date of Patent: Feb. 25, 2020

(54) PROCESS FOR THE GENERATION OF METALLIC FILMS

(71) Applicant: BASF SE, Ludwigshafen am Rhein (DE)

(72) Inventors: Falko Abels, Roemerberg (DE); David Dominique Schweinfurth, Pfungstadt (DE); Karl Matos, Sewickley, PA (US); Daniel Loeffler, Birkenheide (DE); Maraike Ahlf, Schriesheim (DE); Florian Blasberg, Frankfurt (DE); Thomas Schaub, Neustadt (DE); Jan Spielmann, Mannheim (DE); Axel Kirste, Limburgerhof (DE); Boris Gaspar, Stuttgart (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/779,570

(22) PCT Filed: Nov. 29, 2016

(86) PCT No.: PCT/EP2016/079156
§ 371 (c)(1),
(2) Date: May 29, 2018

(87) PCT Pub. No.: WO2017/093265
PCT Pub. Date: Jun. 8, 2017

(65) Prior Publication Data
US 2019/0144998 A1    May 16, 2019

Related U.S. Application Data

(60) Provisional application No. 62/260,672, filed on Nov. 30, 2015.

(30) Foreign Application Priority Data

Dec. 7, 2015  (EP) ..................... 15198196
Feb. 22, 2016 (EP) ..................... 16156733

(51) Int. Cl.
  *C23C 16/455*    (2006.01)
  *C23C 16/06*     (2006.01)
  (Continued)

(52) U.S. Cl.
  CPC .......... *C23C 16/45553* (2013.01); *C07F 7/10* (2013.01); *C07F 9/504* (2013.01);
  (Continued)

(58) Field of Classification Search
  None
  See application file for complete search history.

(56) References Cited

U.S. PATENT DOCUMENTS 6,070,599 A * 6/2000 Ghanayem ............. C23C 16/02
                                                    134/1.3
7,485,340 B2   2/2009 Elers et al.
(Continued)

FOREIGN PATENT DOCUMENTS

EP     1 471 568 A1    10/2004
WO  WO 2015/004315 A1   1/2015

OTHER PUBLICATIONS

Copper(1) carbene hydride complexes acting both as a reducing agent and precursor for Cu ALD: a study through density functional theory (Year: 2013).*

(Continued)

*Primary Examiner* — Mandy C Louie
(74) *Attorney, Agent, or Firm* — Oblon, McClelland, Maier & Neustadt, L.L.P.

(57) ABSTRACT

The present invention is in the field of processes for the generation of thin inorganic films on substrates, in particular
(Continued)

atomic layer deposition processes. It relates to a process for preparing metal films comprising (a) depositing a metal-containing compound from the gaseous state onto a solid substrate and (b) bringing the solid substrate with the deposited metal-containing compound in contact with a reducing agent in the gaseous state, wherein the reducing agent is or at least partially forms at the surface of the solid substrate a carbene, a silylene or a phosphor radical.

9 Claims, 3 Drawing Sheets

(51) Int. Cl.
  *C07F 9/6584* (2006.01)
  *C07F 9/50* (2006.01)
  *C07F 7/10* (2006.01)
  *C07F 9/52* (2006.01)

(52) U.S. Cl.
  CPC ............ *C07F 9/5027* (2013.01); *C07F 9/52* (2013.01); *C07F 9/65848* (2013.01); *C23C 16/06* (2013.01)

(56) References Cited

U.S. PATENT DOCUMENTS

| | | |
|---|---|---|
| 2004/0043149 A1 | 3/2004 | Gordon et al. |
| 2004/0215030 A1* | 10/2004 | Norman .................... C07F 1/00 556/413 |
| 2005/0277780 A1 | 12/2005 | Gordon et al. |
| 2009/0226612 A1 | 9/2009 | Ogawa et al. |
| 2012/0028478 A1 | 2/2012 | Gordon et al. |
| 2012/0323008 A1 | 12/2012 | Barry et al. |
| 2013/0122328 A1 | 5/2013 | Gordon et al. |
| 2013/0189837 A1 | 7/2013 | Haukka et al. |
| 2013/0196502 A1 | 8/2013 | Haukka et al. |
| 2015/0118395 A1 | 4/2015 | Gordon et al. |
| 2016/0087066 A1 | 3/2016 | Gordon et al. |
| 2016/0111276 A1 | 4/2016 | Gordon et al. |
| 2016/0268121 A1 | 9/2016 | Gordon et al. |

OTHER PUBLICATIONS

U.S. Appl. No. 15/114,666, filed Jul. 27, 2016, US 2016-0348243-A1, Xu, K., et al.
U.S. Appl. No. 15/325,840, filed Jan. 12, 2017, US 2017-0175267-A1, Strautmann, J., et al.
U.S. Appl. No. 15/501,631, filed Feb. 3, 2017, US 2017-0233865-A1, Strautmann, J., et al.
U.S. Appl. No. 15/557,178, filed Sep. 11, 2017, US 2018-0044357-A1, Spielmann, J., et al.
U.S. Appl. No. 15/775,856, filed May 14, 2018, Adermann, T., et al.
U.S. Appl. No. 16/063,603, filed Jun. 18, 2018, Abels, F., et al.
U.S. Appl. No. 15/779,893, filed May 30, 2018, Adermann, T., et al.
International Search Report dated Mar. 1, 2017 in PCT/EP2016/079156.
International Preliminary Report on Patentability and Written Opinion dated Jun. 5, 2018 in PCT/EP2016/079156.
Extended European Search Report dated Aug. 11, 2016 in Patent Application No. 15198196.6.
Gangotri Dey, et al., "Copper(I) carbene hydride complexes acting both as reducing agent and precursor for Cu ALD: a study through density functional theory", Theoretical Chemistry Accounts, vol. 133, No. 1, XP035745084, Nov. 2013, 7 pages.
P. Kurpas, et al., "Efficiency of arsenic and phosphorus precursors investigated by reflectance anisotropy spectroscopy", Journal of Crystal Growth, vol. 145, No. 1-4, XP024461883, Dec. 1994, pp. 36-43.
Christoph Heinemann, et al., "Theoretical study of stable silylenes and germylenes", Journal of Organometallic Chemistry, vol. 475, No. 1-2, XP026623422, Jul. 1994, pp. 73-84.
Steven M. George, "Atomic Layer Deposition: An Overview", Chemical Review, vol. 110, No. 1, 2010, pp. 111-131.
Jing Yang, et al., "Direct-liquid-evaporation chemical vapor deposition of smooth, highly conformal cobalt and cobalt nitride thin films", Journal of Materials Chemistry C, vol. 3, 2015, pp. 12098-12106.

* cited by examiner

PROCESS FOR THE GENERATION OF METALLIC FILMS

The present invention is in the field of processes for the generation of thin inorganic films on substrates, in particular atomic layer deposition processes.

With the ongoing miniaturization, e.g. in the semiconductor industry, the need for thin inorganic films on substrates increases while the requirements of the quality of such films become stricter. Thin metal films serve different purposes such as barrier layers, conducting features, or capping layers. Several methods for the generation of metal films are known. One of them is the deposition of film forming compounds from the gaseous state on a substrate. In order to bring metal atoms into the gaseous state at moderate temperatures, it is necessary to provide volatile precursors, e.g. by complexation of the metals with suitable ligands. In order to convert deposited metal complexes to metal films, it is usually necessary to expose the deposited metal complex to a reducing agent.

Typically, hydrogen gas is used to convert deposited metal complexes to metal films. While hydrogen works reasonably well as reducing agent for relatively noble metals like copper or silver, it does not yield satisfactory results for less noble metals such as titanium or aluminum.

WO 2015/0 004 315 A1 discloses a reducing agents with a quinoid structure. However, these reducing agents leave a significant amount of impurities in the metal film which is unfavorable for some applications, for example microchip production.

Dey et al. disclose in Theoretical Chemistry Accounts, volume 133 (2013), page 1 to 7 copper(I) carbene hydride complexes acting as reducing agent in atomic layer deposition. However, for high purity metal films copper traces can be detrimental to device performance.

It was therefore an object of the present invention to provide reducing agents, which are capable of reducing surface-bound metal atoms to the metallic state leaving less impurity in the metal film. The reducing agents should be easy to handle; in particular, it should be possible to vaporize them with as little decomposition as possible. Furthermore, the reducing agent should be versatile, so it can be applied to a broad range of different metals including electropositive metals.

These objects were achieved by a process for preparing metal films comprising
(a) depositing a metal-containing compound from the gaseous state onto a solid substrate and
(b) bringing the solid substrate with the deposited metal-containing compound in contact with a reducing agent in the gaseous state or in solution,
wherein the reducing agent is or at least partially forms at the surface of the solid substrate a carbene, a silylene or a phosphor radical,
wherein the carbene is a compound of general formula (I), (II), (IVa), (IVb), (Va) or (Vb)

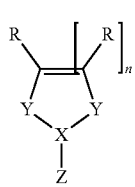
(I)

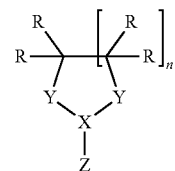
(II)

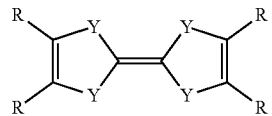
(IVa)

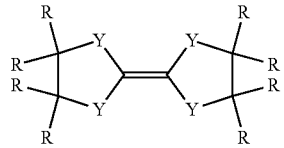
(IVb)

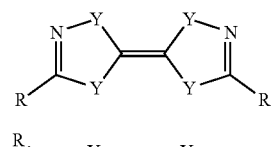
(Va)

(Vb)

wherein R is hydrogen, an alkyl, alkenyl, aryl, or silyl group
X is C, Si, or P,
Y is S, NR, or $CR_2$,
Z is nothing, H, alkyl, halogen, an amine, $PR_2$ or a boron species, and
n is 0, 1 or 2.

The present invention further relates to the use of a carbene, silylene, or phosphor radical as reducing agent in an atomic layer deposition process, wherein the carbene is a compound of general formula (I), (II), (IVa), (IVb), (Va) or (Vb).

Preferred embodiments of the present invention can be found in the description and the claims. Combinations of different embodiments fall within the scope of the present invention.

The process according to the present invention is for preparing metal films. Metal films in the context of the present invention are as generally used in the art metal-containing films with high electrical conductivity, usually at least $10^4$ S/m, preferably at least $10^5$ S/m, in particular at least $10^6$ S/m.

The process according to the present invention includes depositing a metal-containing compound from the gaseous state onto a solid substrate. The metal-containing compound contains at least one metal atom. Metals include Li, Be, Na, Mg, Al, K, Ca, Sc, Ti, V, Cr, Mn, Fe, Co, Ni, Cu, Zn, Ga, Rb, Sr, Y, Zr, Nb, Mo, Tc, Ru, Rh, Pd, Ag, Cd, In, Sn, Cs, Ba, La, Ce, Pr, Nd, Pm, Sm, Eu, Gd, Tb, Dy, Ho, Er, Tm, Yb, Lu, Hf, Ta, W, Re, Os Ir, Pt, Au, Hg, Tl, Bi. Preferably, the metal-containing compound contains a metal which is more electropositive than Cu, more preferably more electropositive than Ni. In particular, the metal-containing compound contains Ti, Ta, Mn, Mo, W, or Al. It is possible that more than one metal-containing compound is deposited on the surface, either simultaneously or consecutively. If more than one metal-containing compound is deposited on a solid substrate it is possible that all metal-containing compounds contain the same metal or different ones, preferably they contain the same metal.

Any metal-containing compound, which can be brought into the gaseous state, is suitable. These compounds include alkyl metals such as dimethyl zinc, trimethylaluminum; metal alkoxylates such as tetramethoxy silicon, tetra-isopropoxy zirconium or tetra-iso-propoxy titanium; cyclopentadiene complexes like pentamethylcyclopendienyl-trimethoxy titanium or di(ethylcycopentadienyl) manganese; metal carbenes such as tantalum-pentaneopentylat or bisimidazolidinylen ruthenium chloride; metal halogenides such as tantalum pentachloride or titanium tetrachloride; carbon monoxide complexes like hexacarbonyl chromium or tetracarbonyl nickel; amine complexes such as di-(bis-tertbuylamino)-di-(bismethylamino) molybdenum, di-(bistertbuylamino)-di-(bismethylamino) tungsten or tetra-dimethylamino titanium; dione complexes such as tri-acetylacetonato aluminum or bis(2,2,6,6-tetramethyl-3,5-heptanedionato) manganese. Alkyl metals, cyclopentadiene complexes, metal halogenides and amine complexes are preferred. It is preferred that the molecular weight of the metal-containing compound is up to 1000 g/mol, more preferred up to 800 g/mol, in particular up to 600 g/mol, such as up to 500 g/mol.

The solid substrate can be any solid material. These include for example metals, semimetals, oxides, nitrides, and polymers. It is also possible that the substrate is a mixture of different materials. Examples for metals are aluminum, steel, zinc, and copper. Examples for semimetals are silicon, germanium, and gallium arsenide. Examples for oxides are silicon dioxide, titanium dioxide, and zinc oxide. Examples for nitrides are silicon nitride, aluminum nitride, titanium nitride, and gallium nitride. Examples for polymers are polyethylene terephthalate (PET), polyethylene naphthalene-dicarboxylic acid (PEN), and polyamides.

The solid substrate can have any shape. These include sheet plates, films, fibers, particles of various sizes, and substrates with trenches or other indentations. The solid substrate can be of any size. If the solid substrate has a particle shape, the size of particles can range from below 100 nm to several centimeters, preferably from 1 µm to 1 mm. In order to avoid particles or fibers to stick to each other while the metal-containing compound is deposited onto them, it is preferably to keep them in motion. This can, for example, be achieved by stirring, by rotating drums, or by fluidized bed techniques.

According to the present invention the solid substrate with the deposited metal-containing compound is brought in contact with a reducing agent in the gaseous state, wherein the reducing agent is or at least partially forms at the surface of the solid substrate a carbene, a silylene or a phosphor radical. By doing so, the deposited metal-containing compound is reduced to elemental metal. It was surprisingly found that carbenes, silylenes or phosphor radicals work very efficiently in reducing even electropositive metals while leaving a very low amount of contaminants in the metal film. Some reducing agents which do not contain a carbene, silylene or phosphor radical, form these upon heating, for example to at least 50° C., preferably at least 80° C., more preferably at least 120° C., such as at least 150° C. or at least 180° C. The term "partially" typically means that at thermodynamic equilibrium under given conditions at least 5 mol-% of the reducing agent has formed a carbene, silylene or phosphor radical, preferably at least 10 mol-%, more preferably at least 20 mol-%, in particular at least 50 mol-%. It is also possible, that the reducing agent only at least partially forms a carbene, silylene or phosphor radical upon contact with the solid substrate with the deposited metal-containing compound.

The reducing agent has a low tendency to form a permanent bond with the surface of the solid substrate with the deposited metal-containing compound. As a result, the metal film hardly gets contaminated with the reaction products of the reducing agent. Preferably, less than 5 weight-% reducing agent with regard to the metal film remains in the metal film, more preferably less than 1 wt.-%, in particular less than 0.1 wt.-%, such as 0.01 wt.-%.

R in the compound of general formula (I) and (II) can be the same or different to each other if more than one R is present in the compound of general formula (I) or (II). It is possible that two or more R form together a ring, which can be aliphatic or aromatic and which can be substituted.

An alkyl group can be linear or branched. Examples for a linear alkyl group are methyl, ethyl, n-propyl, n-butyl, n-pentyl, n-hexyl, n-heptyl, n-octyl, n-nonyl, n-decyl. Examples for a branched alkyl group are iso-propyl, iso-butyl, sec-butyl, tert-butyl, 2-methyl-pentyl, 2-ethyl-hexyl, cyclopropyl, cyclohexyl, indanyl, norbornyl. Preferably, the alkyl group is a $C_1$ to $C_8$ alkyl group, more preferably a $C_1$ to $C_6$ alkyl group, in particular a $C_1$ to $C_4$ alkyl group, such as methyl or ethyl.

An alkenyl group contains at least one carbon-carbon double bond. The double bond can include the carbon atom with which R is bound to the rest of the molecule, or it can be placed further away from the place where R is bound to the rest of the molecule. Alkenyl groups can be linear or branched. Examples for linear alkenyl groups in which the double bond includes the carbon atom with which R is bound to the rest of the molecule include 1-ethenyl, 1-propenyl, 1-n-butenyl, 1-n-pentenyl, 1-n-hexenyl, 1-n-heptenyl, 1-n-octenyl. Examples for linear alkenyl groups in which the double bond is placed further away from the place where R is bound to the rest of the molecule include 1-n-propen-3-yl, 2-buten-1-yl, 1-buten-3-yl, 1-buten-4-yl, 1-hexen-6-yl. Examples for branched alkenyl groups in which the double bond includes the carbon atom with which R is bound to the rest of the molecule include 1-propen-2-yl, 1-n-buten-2-yl, 2-buten-2-yl, cyclopenten-1-yl, cyclohexen-1-yl. Examples for branched alkenyl groups in which the double bond is placed further away from the place where R is bound to the rest of the molecule include 2-methyl-1-buten-4-yl, cyclo-penten-3-yl, cyclohexene-3-yl. Examples for an alkenyl group with more than one double bonds include 1,3-buta-dien-1-yl, 1,3-butadien-2-yl, cylopentadien-5-yl.

Aryl groups include aromatic hydrocarbons such as phenyl, naphthalyl, anthrancenyl, phenanthrenyl groups and heteroaromatic groups such as pyrryl, furanyl, thienyl, pyridinyl, quinoyl, benzofuryl, benzothiophenyl, thienothienyl. Several of these groups or combinations of these groups are also possible like biphenyl, thienophenyl or furanylthienyl. Aryl groups can be substituted for example by halogens like fluoride, chloride, bromide, iodide; by pseudohalogens like cyanide, cyanate, thiocyanate; by alcohols; alkyl chains or alkoxy chains. Aromatic hydrocarbons are preferred, phenyl is more preferred.

A silyl group is a silicon atom with typically three substituents. Preferably a silyl group has the formula $SiA_3$, wherein A is independent of each other hydrogen, an alkyl group, an aryl group or a silyl group. It is possible that all three A are the same or that two A are the same and the remaining A is different or that all three A are different to each other, preferably all A are the same. Alkyl and aryl groups are as described above. Examples for siliyl groups include SiH$_3$, methylsilyl, trimethylsilyl, triethylsilyl, tri-n-propylsilyl, tri-iso-propylsilyl, tricyclohexylsilyl, dimethyl-tert-butylsilyl, dimethylcyclohexylsilyl, methyl-di-iso-propylsilyl, triphenylsilyl, phenylsilyl, dimethylphenylsilyl, pentamethyldisilyl.

Preferably, Y in the compound of general formula (I) or (II) is S or NR if X is C, wherein R has the same definition as above. More preferably, Y is NR. n is preferably 1.

Z in the compound of general formula (I) or (II) is nothing, H, alkyl, halogen, an amine, PR$_2$ or a boron species. Alkyl groups are as described above. Halogens include fluorine, chlorine, bromine, iodine, preferably chlorine. Amines are preferably doubly substituted, for example by two alkyl groups, aryl groups or silyl groups as described above. A preferred amine is hexamethyldisilylamine. Z is preferably nothing or hydrogen, in particular nothing.

Preferred examples for the compound of general formula (I) or (II), in which X is silicon are given below.

I-Si-1

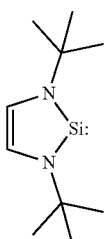

I-Si-2

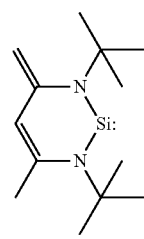

I-Si-3

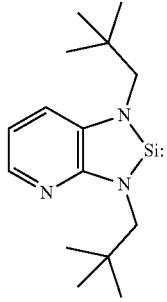

I-Si-4

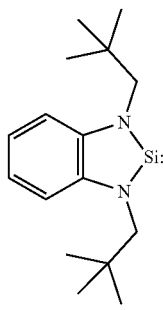

I-Si-5

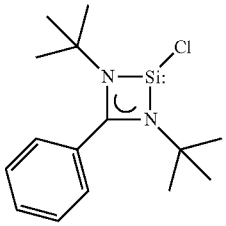

I-Si-6

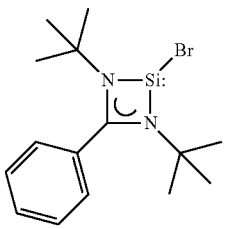

I-Si-7

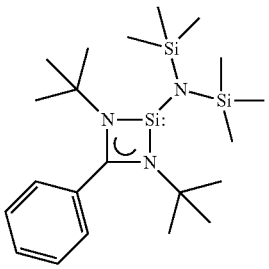

I-Si-8

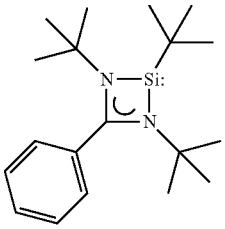

I-Si-9

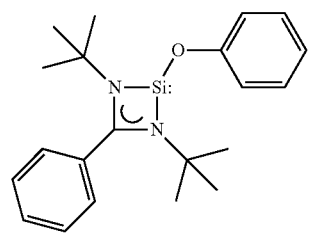

I-Si-10

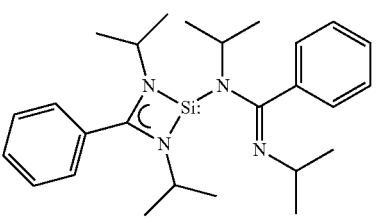

II-Si-11

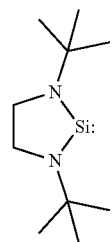

II-Si-12

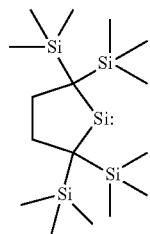

If Z is PR$_2$, R has the same definition as above. A boron species is any group which contains a boron atom, wherein the boron atom is bound to X. Preferably, if Z in the reducing agent of general formula (I) is a boron species, the reducing agent is a compound of general formula (Ia), (Ib), (Ic), (Id), (Ie), or (If).

(Ia)

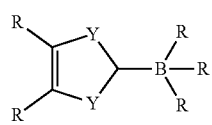

(Ib)

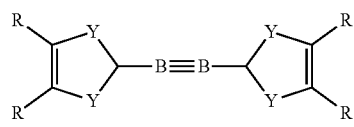

(Ic)

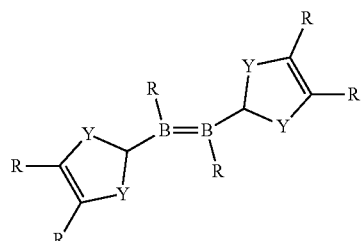

(Id)

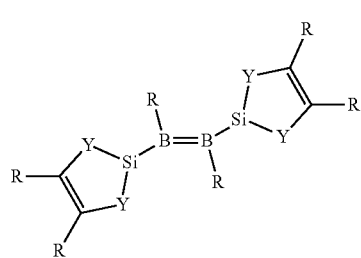

(Ie)

(If)

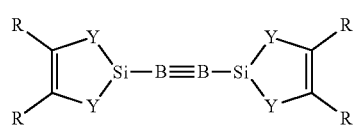

The definitions for R and Y are the same as above. As already described for general formula (I), R in any of the general formulae (Ia), (Ib), (Ic), (Id), (Ie), or (If) can be the same or different to each other, including the case that some R are the same and the remaining are different to these. The reducing agents of general formula (Ia), (Ib), (Ic), (Id), (Ie), or (If) at least partially form carbene compounds upon heating and/or contact with a metal-containing compound. Preferably, R which is bond to a boron atom in the general formula (Ia), (Ib), (Ic), (Id), (Ie), or (If) is hydrogen.

Another preferred possibility for reducing agents which at least partially form phosphor radicals upon heating and/or contact with a metal-containing compound are compounds of general formula (III).

(III)

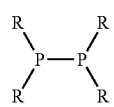

The definition of R is the same as above including the fact that the different R can be the same or different to each other.

Some preferred examples of compounds of general formula (III) are shown below.

III-1

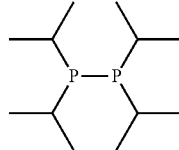

III-2

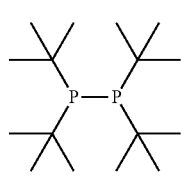

III-3

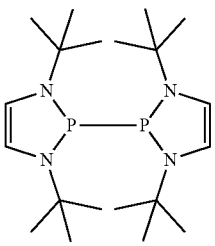

Another preferred possibility for reducing agents are compounds of general formula (IVa) or compounds of general formula (IVb).

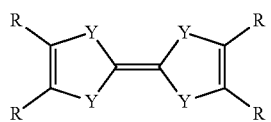
(IVa)
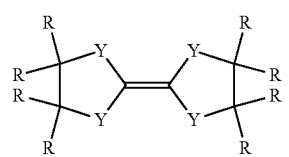
(IVb)
The definition of R is the same as above including the fact that the different R can be the same or different to each other.
Some preferred examples of compounds of general formula (IVa) are shown below.
IVa-1
IVa-2
IVa-3
IVa-4
IVa-5
IVa-6
IVa-7
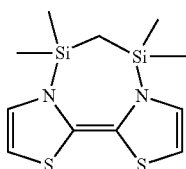
IVa-8
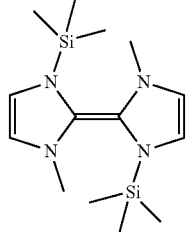
IVa-9
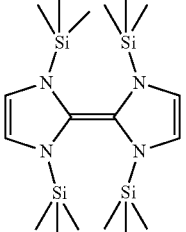
IVa-10
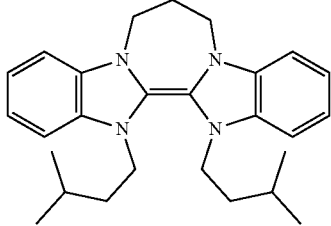
IVa-11
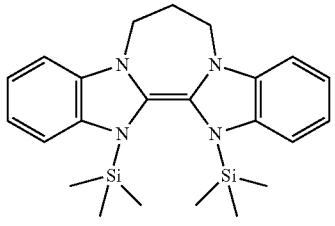
IVa-12
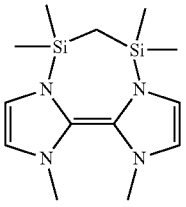
IVa-13
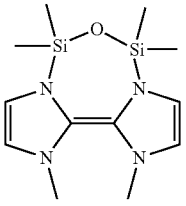
IVa-14

Another preferred possibility for reducing agents are compounds of general formula (Va) or compounds of general formula (Vb)

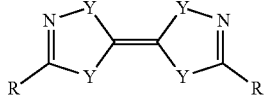
(Va)

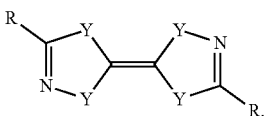
(Vb)

The definition of R is the same as above including the fact that the different R can be the same or different to each other.

Some preferred examples of compounds of general formula (Va) are shown below.

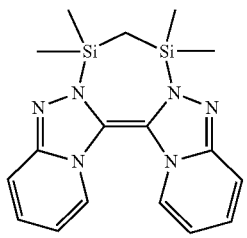
Va-1

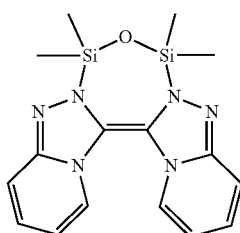
Va-2

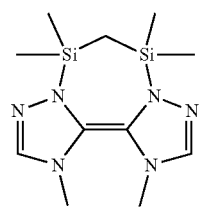
Va-3

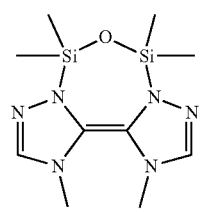
Va-4

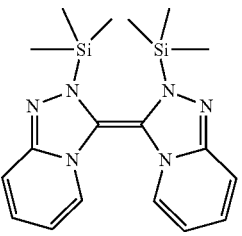
Va-5

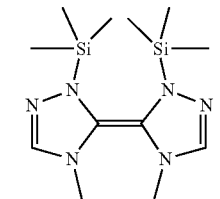
Va-6

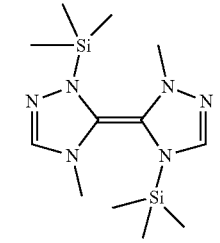
Va-7

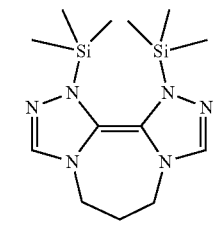
Va-8

Both the metal-containing compound and the reducing agent used in the process according to the present invention are used at high purity to achieve the best results. High purity means that the substance used contains at least 90 wt.-% metal-containing compound or reducing agent, preferably at least 95 wt.-%, more preferably at least 98 wt.-%, in particular at least 99 wt.-%. The purity can be determined by elemental analysis according to DIN 51721 (Prüfung fester Brennstoffe—Bestimmung des Gehaltes an Kohlenstoff and Wasserstoff—Verfahren nach Radmacher-Hoverath, August 2001).

In the process according to the present invention the metal-containing compound and the reducing agent are deposited or brought in contact to the surface from the gaseous state. They can be brought into the gaseous state for example by heating them to elevated temperatures. In any case a temperature below the decomposition temperature of the metal-containing compound or the reducing agent has to be chosen. In this context, the formation of silylenes, carbenes or phosphor radicals is not regarded as decomposition. In contrast, decomposition is a reaction in which the metal-containing compound or the reducing agent is converted to an undefined variety of different compounds. Preferably, the heating temperature ranges from 0° C. to 300° C., more preferably from 10° C. to 250° C., even more preferably from 20° C. to 200° C., in particular from 30° C. to 150° C.

Another way of bringing the metal-containing compound or the reducing agent into the gaseous state is direct liquid injection (DLI) as described for example in US 2009/0 226 612 A1. In this method the metal-containing compound or the reducing agent is typically dissolved in a solvent and sprayed in a carrier gas or vacuum. If the vapor pressure of metal-containing compound or the reducing agent and the temperature are sufficiently high and the pressure is sufficiently low the metal-containing compound or the reducing agent is brought into the gaseous state. Various solvents can be used provided that the metal-containing compound or the reducing agent shows sufficient solubility in that solvent such as at least 1 g/l, preferably at least 10 g/l, more preferably at least 100 g/l. Examples for these solvents are coordinating solvents such as tetrahydrofuran, dioxane, diethoxyethane, pyridine or non-coordinating solvents such as hexane, heptane, benzene, toluene, or xylene. Solvent mixtures are also suitable.

Alternatively, the metal-containing compound or the reducing agent can be brought into the gaseous state by direct liquid evaporation (DLE) as described for example by J. Yang et al. (Journal of Materials Chemistry, 2015). In this method, the metal-containing compound or the reducing agent is mixed with a solvent, for example a hydrocarbon such as tetradecane, and heated below the boiling point of the solvent. By evaporation of the solvent, the metal-containing compound or the reducing agent is brought into the gaseous state. This method has the advantage that no particulate contaminants are formed on the surface.

It is preferred to bring the metal-containing compound or the reducing agent into the gaseous state at decreased pressure. In this way, the process can usually be performed at lower heating temperatures leading to decreased decomposition of the metal-containing compound or the reducing agent. It is also possible to use increased pressure to push the metal-containing compound or the reducing agent in the gaseous state towards the solid substrate. Often, an inert gas, such as nitrogen or argon, is used as carrier gas for this purpose. Preferably, the pressure is 10 bar to $10^{-7}$ mbar, more preferably 1 bar to $10^{-3}$ mbar, in particular 1 to 0.01 mbar, such as 0.1 mbar.

It is also possible that the reducing agent is brought in contact with the solid substrate in solution. Bringing the reducing agent in contact with the solid substrate in solution is advantageous for compounds which are not stable enough for evaporation. However, the solution needs to have a high purity to avoid undesirable contaminations on the surface. Contacting from solution usually requires a solvent which does not react with the reducing agent. Examples for solvents are ethers like diethyl ether, methyl-tert-butylether, tetrahydrofurane, dioxane; ketones like acetone, methylethylketone, cyclopentanone; esters like ethyl acetate; lactones like 4-butyrolactone; organic carbonates like diethylcarbonate, ethylene carbonate, vinylenecarbonate; aromatic hydrocarbons like benzene, toluene, xylene, mesitylene, ethylbenzene, styrene; aliphatic hydrocarbons like n-pentane, n-hexane, cyclohexane, iso-undecane, decaline, hexadecane. Ethers are preferred, in particular tetrahydrofurane. The concentration of the reducing agent depends among others on the reactivity and the desired reaction time. Typically, the concentration is 0.1 mmol/l to 10 mol/l, preferably 1 mmol/l to 1 mol/l, in particular 10 to 100 mmol/l.

The deposition of the metal-containing compound takes place if the substrate comes in contact with the metal-containing compound. Generally, the deposition process can be conducted in two different ways: either the substrate is heated above or below the decomposition temperature of the metal-containing compound. If the substrate is heated above the decomposition temperature of the metal-containing compound, the metal-containing compound continuously decomposes on the surface of the solid substrate as long as more metal-containing compound in the gaseous state reaches the surface of the solid substrate. This process is typically called chemical vapor deposition (CVD). Usually, an inorganic layer of homogeneous composition, e.g. the metal oxide or nitride, is formed on the solid substrate as the organic material is desorbed from the metal M. This inorganic layer is then converted to the metal layer by bringing it in contact to the reducing agent which is or at least partially forms at the surface of the solid substrate a carbene, a silylene or a phosphor radical. Typically the solid substrate is heated to a temperature in the range of 300 to 1000° C., preferably in the range of 350 to 600° C.

Alternatively, the substrate is below the decomposition temperature of the metal-containing compound. Typically, the solid substrate is at a temperature equal to or lower than the temperature of the place where the metal-containing compound is brought into the gaseous state, often at room temperature or only slightly above. Preferably, the temperature of the substrate is at least 30° C. lower than the place where the metal-containing compound is brought into the gaseous state. Preferably, the temperature of the substrate is from room temperature to 400° C., more preferably from 100 to 300° C., such as 150 to 220° C.

The deposition of metal-containing compound onto the solid substrate is either a physisorption or a chemisorption process. Preferably, the metal-containing compound is chemisorbed on the solid substrate. One can determine if the metal-containing compound chemisorbs to the solid substrate by exposing a quartz microbalance with a quartz crystal having the surface of the substrate in question to the metal-containing compound in the gaseous state. The mass increase is recorded by the eigen frequency of the quartz crystal. Upon evacuation of the chamber in which the quartz crystal is placed the mass should not decrease to the initial mass, but about a monolayer of the residual metal-containing compound remains if chemisorption has taken place. In most cases where chemisorption of the metal-containing compound to the solid substrate occurs, the x-ray photoelectron spectroscopy (XPS) signal (ISO 13424 EN—Surface chemical analysis—X-ray photoelectron spectroscopy—Reporting of results of thin-film analysis; October 2013) of M changes due to the bond formation to the substrate.

If the temperature of the substrate in the process according to the present invention is kept below the decomposition temperature of the metal-containing compound, typically a monolayer is deposited on the solid substrate. Once a molecule of the metal-containing compound is deposited on the solid substrate further deposition on top of it usually becomes less likely. Thus, the deposition of the metal-containing compound on the solid substrate preferably represents a self-limiting process step. The typical layer thickness of a self-limiting deposition processes step is from 0.01 to 1 nm, preferably from 0.02 to 0.5 nm, more preferably from 0.03 to 0.4 nm, in particular from 0.05 to 0.2 nm. The layer thickness is typically measured by ellipsometry as described in PAS 1022 DE (Referenzverfahren zur Bestimmung von optischen and dielektrischen Materialeigenschaften sowie der Schichtdicke dünner Schichten mittels Ellipsometrie; February 2004).

A deposition process comprising a self-limiting process step and a subsequent self-limiting reaction is often referred to as atomic layer deposition (ALD). Equivalent expressions are molecular layer deposition (MLD) or atomic layer epitaxy (ALE). Hence, the process according to the present invention is preferably an ALD process. The ALD process is described in detail by George (Chemical Reviews 110 (2010), 111-131).

A particular advantage of the process according to the present invention is that the compound of general formula (I) is very versatile, so the process parameters can be varied in a broad range. Therefore, the process according to the present invention includes both a CVD process as well as an ALD process.

Preferably, after deposition of a metal-containing compound on the solid substrate and before bringing the solid substrate with the deposited metal-containing compound in contact with a reducing agent, the solid substrate with the deposited metal-containing compound is brought in contact to an acid in the gaseous phase. Without being bound by a theory, it is believed that the protonation of the ligands of the metal-containing compound facilitates its decomposition and reduction. Preferably, carboxylic acids are used such as formic acid, acetic acid, propionic acid, butyric acid, or trifluoroacetic acid, in particular formic acid.

Often it is desired to build up thicker layers than those just described. In order to achieve this the process comprising (a) and (b), which can be regarded as one ALD cycle, are preferably performed at least twice, more preferably at least 10 times, in particular at least 50 times. Usually, the process comprising (a) and (b) is performed not more than 1000 times.

The deposition of the metal-containing compound or its contacting with a reducing agent can take from milliseconds to several minutes, preferably from 0.1 second to 1 minute, in particular from 1 to 10 seconds. The longer the solid substrate at a temperature below the decomposition temperature of the metal-containing compound is exposed to the metal-containing compound the more regular films formed with less defects. The same applies for contacting the deposited metal-containing compound to the reducing agent.

The process according to the present invention yields a metal film. A film can be only one monolayer of a metal or be thicker such as 0.1 nm to 1 μm, preferably 0.5 to 50 nm. A film can contain defects like holes. These defects, however, generally constitute less than half of the surface area covered by the film. The film preferably has a very uniform film thickness which means that the film thickness at different places on the substrate varies very little, usually less than 10%, preferably less than 5%. Furthermore, the film is preferably a conformal film on the surface of the substrate. Suitable methods to determine the film thickness and uniformity are XPS or ellipsometry.

The film obtained by the process according to the present invention can be used in an electronic element. Electronic elements can have structural features of various sizes, for example from 100 nm to 100 μm. The process for forming the films for the electronic elements is particularly well suited for very fine structures. Therefore, electronic elements with sizes below 1 μm are preferred. Examples for electronic elements are field-effect transistors (FET), solar cells, light emitting diodes, sensors, or capacitors. In optical devices such as light emitting diodes or light sensors the film obtained by the process according to the present invention serves to increase the reflective index of the layer which reflects light.

Preferred electronic elements are transistors. Preferably the film acts as chemical barrier metal in a transistor. A chemical barrier metal is a material reduces diffusion of adjacent layers while maintaining electrical connectivity.

EXAMPLES

Example 1

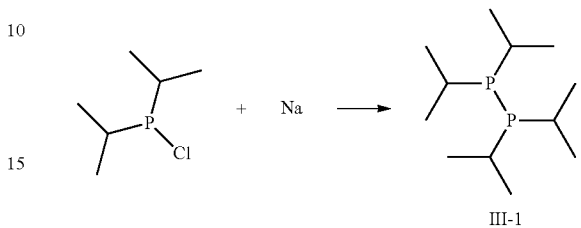

III-1

Sodium (4.1 g, 0.18 mol) was added to a solution of degassed, dry dibutylether (150 ml) under inert conditions. The reaction mixture was heated to 110° C. and chloro-di-isopropylphosphine added slowly (25 g, 0.16 mol). After addition, the mixture was stirred for another 2 h at 110° C. Subsequently, 80 mL degassed, distilled water was added carefully. Phases were separated and organic layer washed with degassed, distilled water. Organic phase was dried over $Na_2SO_4$, filtered off the drying agent and distilled to yield the pure compound III-1.

Boiling point: 74-75° C. at 0.75 mbar

Figure 1:
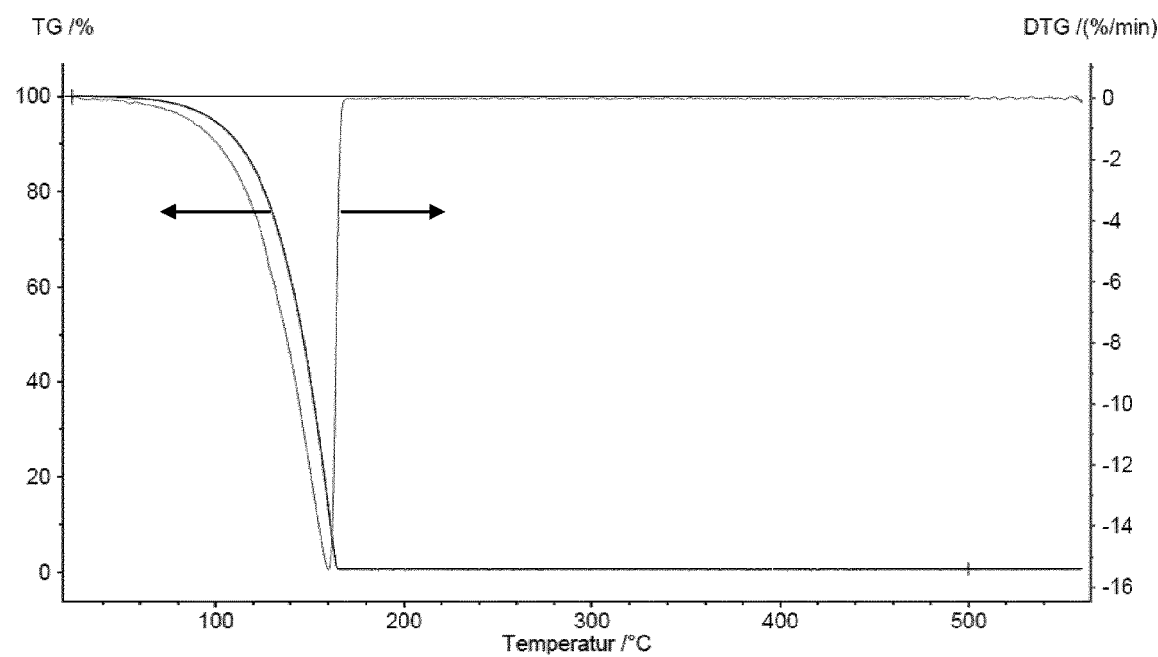
FIGS. 1, 4, and 5 show thermal gravimetry analysis data of the compounds in the examples.
Figure 2:
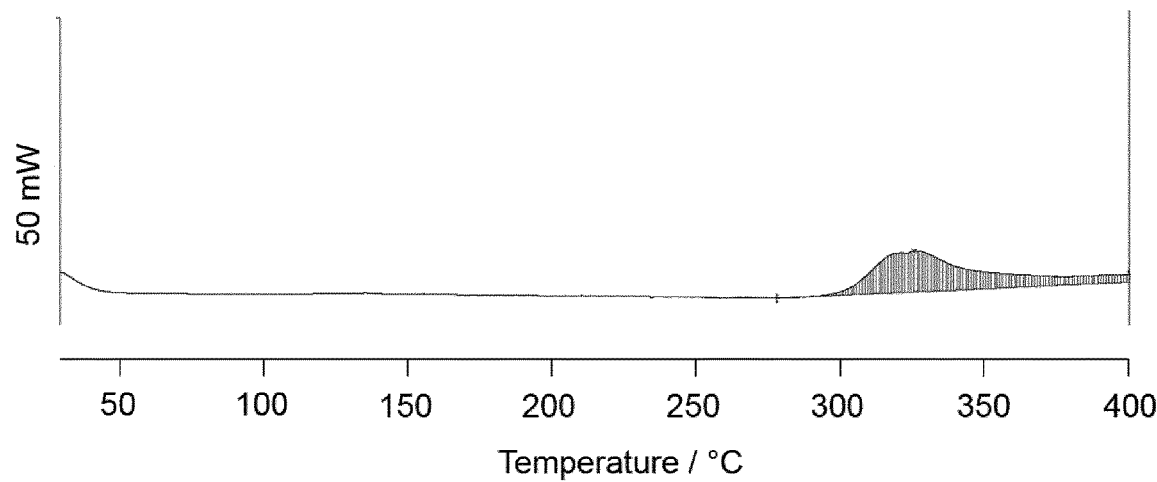
FIGS. 2, 3, and 6 show differential scanning calorimetry data of the compound in the examples.

The result of the thermal gravimetry (TG) analysis including the relative mass loss per minute (DTG) is shown in FIG. 1. The fact that less then 1% mass remain at 200° C. indicate that compound III-1 evaporates completely without decomposition. The differential scanning calorimetry (DSC) data depicted in FIG. 2 support this fact, as the first sign of a reaction occurs at 279° C.

Example 2

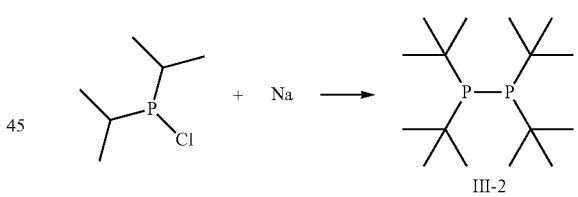

III-2

Sodium (3.5 g, 0.15 mol) was added to a solution of degassed, dry dibutylether (150 ml) under inert conditions. The reaction mixture was heated to 110° C. and chloro-di-isopropylphosphine added slowly (25 g, 0.14 mol). After addition, the mixture was stirred for another 2 h at 110° C. Subsequently, 80 mL degassed, distilled water was added carefully. Phases were separated and organic layer washed with degassed, distilled water. Organic phase was dried over $Na_2SO_4$, filtered off the drying agent and distilled to yield the pure compound III-2.

Boiling point: 117° C. at 0.5 mbar

Figure 3:
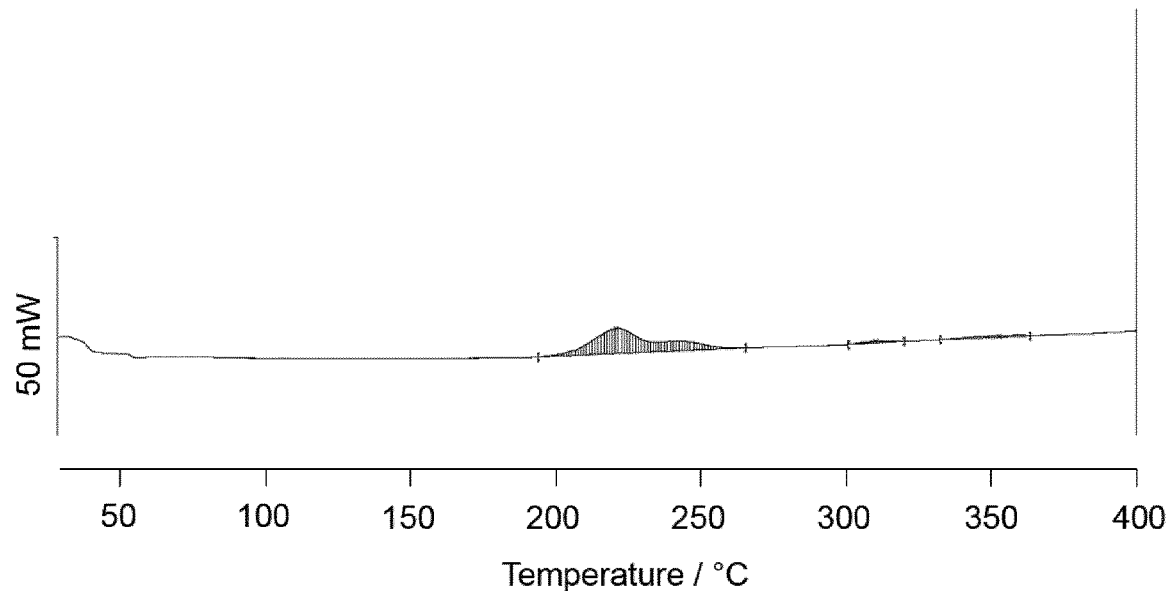

In the DSC curve depicted in FIG. 3, a first sign of a reaction occurs at 195° C. indicating that compound III-2 can be evaporated without decomposition.

Example 3

Figure 4:
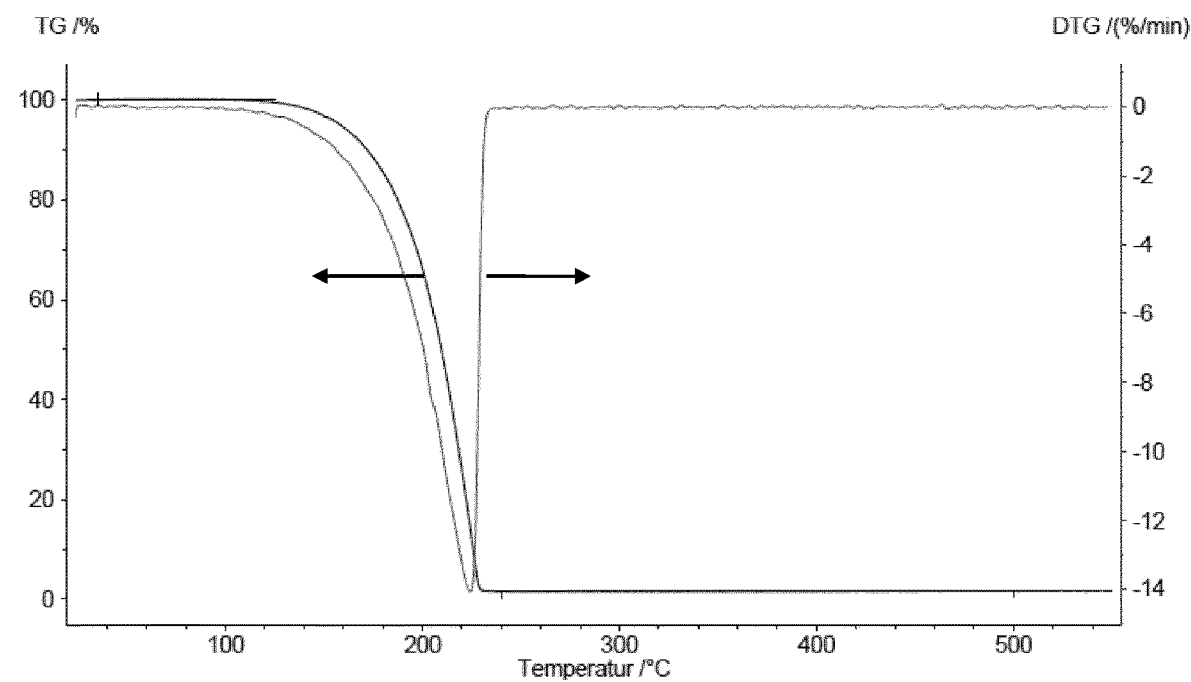

A TG analysis was performed on compound IV-1. The result is depicted in FIG. 4. A mass loss of 98.5% between 35° C. and 250° C. indicates that compound IV-1 can be evaporated without decomposition.

Example 4

Figure 5:
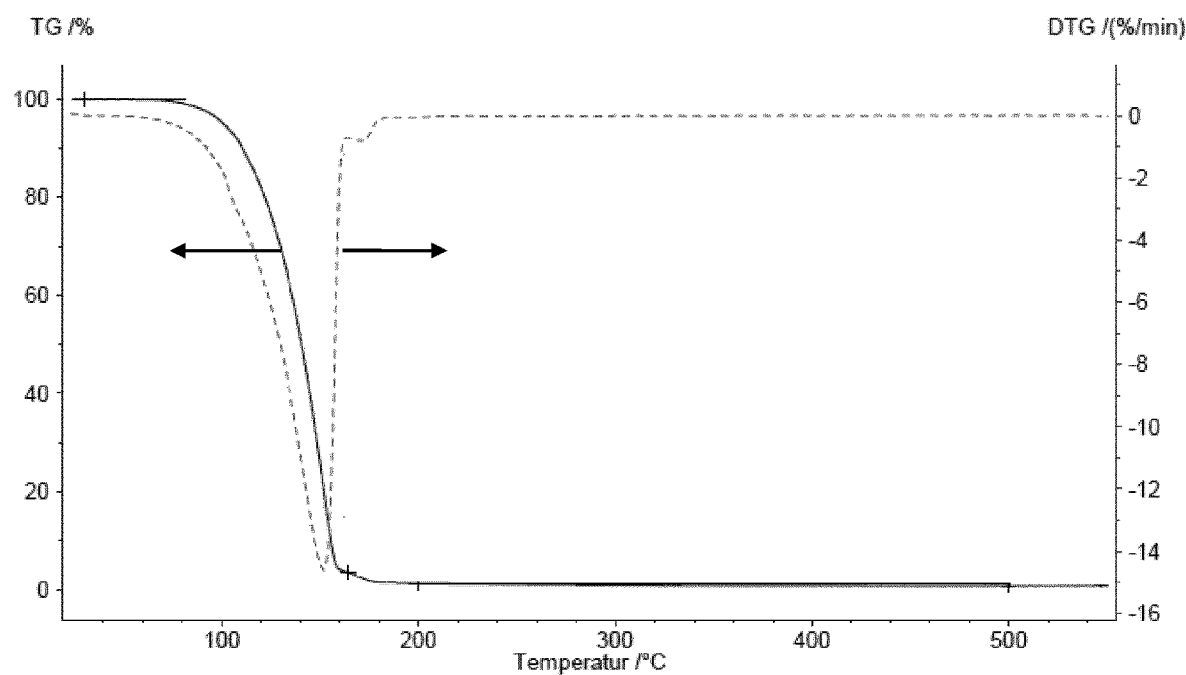
Figure 6:
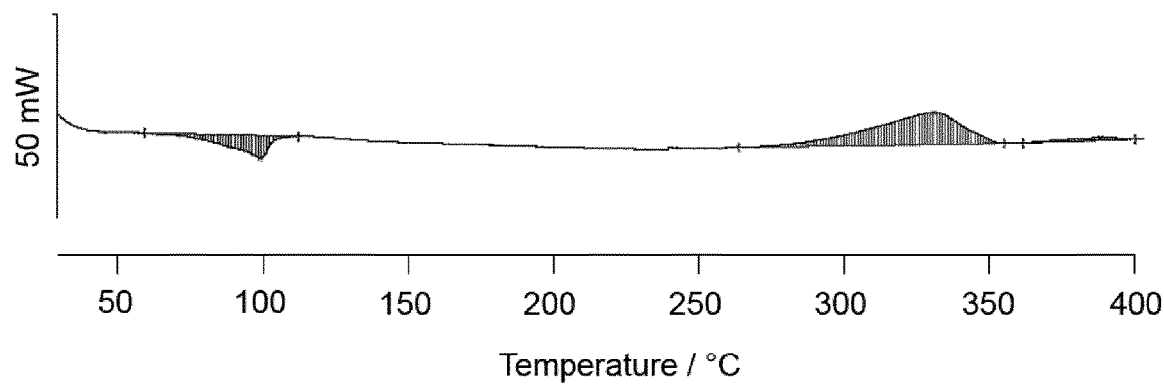

A TG analysis was performed on compound I-Si-1. The result is depicted in FIG. 5. A mass loss of 98.8% between 25° C. and 200° C. indicates that compound I-Si-1 can be evaporated without decomposition. The vapor pressure of compound I-Si-1 was measured to be 1 mbar at 80° C. FIG. 6 shows the DSC curve with an endothermic peak in the range of 60° C. to 100° C. and an exothermic peak above 260° C. which can be attributed to decomposition.

The invention claimed is:

1. A process for preparing a metal film, comprising:
   (a) depositing a metal-containing compound from the gaseous state onto a solid substrate; and
   (b) bringing the solid substrate with the deposited metal-containing compound in contact with a reducing agent in the gaseous state or in solution,
   wherein the reducing agent is or at least partially forms at the surface of the solid substrate a carbene, a silylene or a phosphor radical,
   wherein the carbene is a compound of formula (I), (II), (IVa), (IVb), (Va) or (Vb);

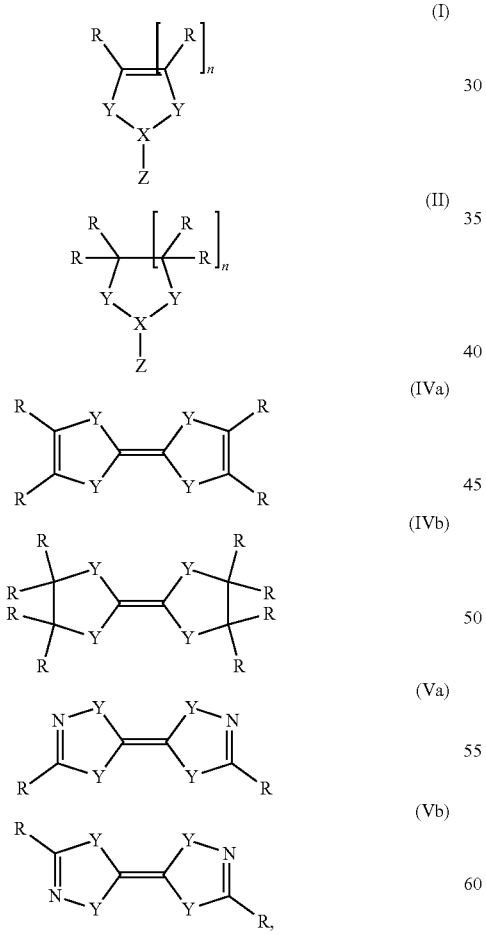

wherein R is hydrogen, an alkyl, alkenyl, aryl, or silyl group
X is C, Si, or P,
Y is S, NR, or $CR_2$,
Z is nothing, H, alkyl, halogen, an amine, $PR_2$ or a boron species, and
n is 0, 1 or 2.

2. The process according to claim 1, wherein the reducing agent is a compound of formula (Ia), (Ib), (Ic), (Id), (Ie), or (If):

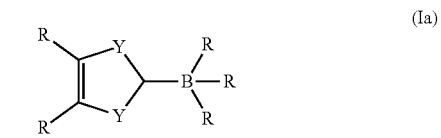

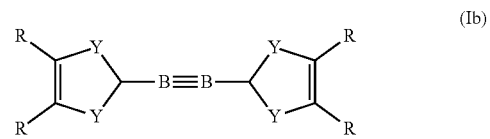

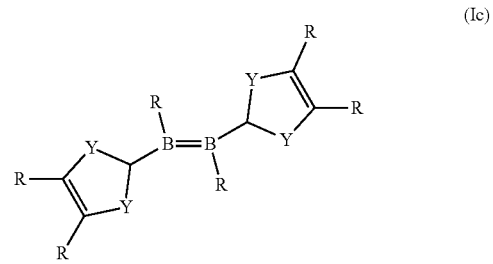

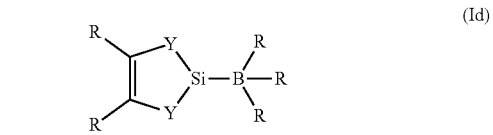

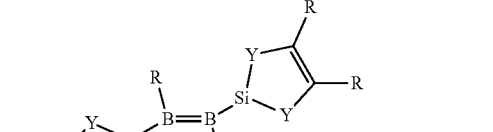

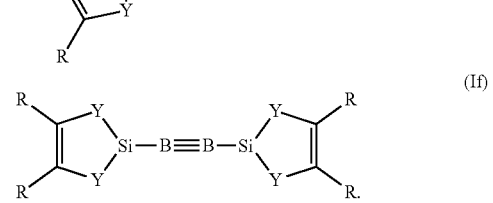

3. The process according to claim 1, wherein the reducing agent is a compound of formula (III):

4. The process according to claim 1, wherein the reducing agent is a compound of formula (IVa) or a compound of formula (IVb):

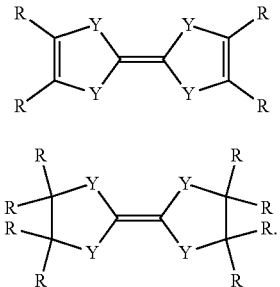

(IVa)

(IVb)

5. The process according to claim 1, wherein the reducing agent is a compound of formula (Va) or a compound of formula (Vb):

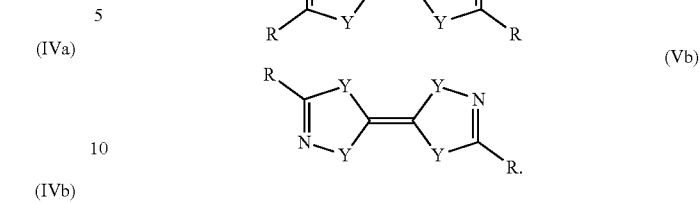

(Va)

(Vb)

6. The process according to claim 1, wherein the reducing agent has a vapor pressure of at least 0.1 mbar at 200° C.

7. The process according to claim 1, wherein (a) and (b) are successively performed at least twice.

8. The process according to claim 1, wherein the metal-containing compound comprises Ti, Ta, Mn, Mo, W, or Al.

9. The process according to claim 1, wherein the temperature does not exceed 350° C.

* * * * *

UNITED STATES PATENT AND TRADEMARK OFFICE
CERTIFICATE OF CORRECTION

Page 1 of 2

PATENT NO. : 10,570,514 B2
APPLICATION NO. : 15/779570
DATED : February 25, 2020
INVENTOR(S) : Falko Abels et al.

It is certified that error appears in the above-identified patent and that said Letters Patent is hereby corrected as shown below:

On the Title Page

In the illustrative figure, Line 9 (approx.), delete "Temperatur" and insert -- Temperature --.

In the Drawings

In sheet 1 of 3, FIG. 1, Line 9 (approx.), delete "Temperatur" and insert -- Temperature --.

In sheet 2 of 3, FIG. 4, Line 9 (approx.), delete "Temperatur" and insert -- Temperature --.

In sheet 3 of 3, FIG. 5, Line 9 (approx.), delete "Temperatur" and insert -- Temperature --.

In the Specification

In Column 2, Line 60, delete "Os Ir" and insert -- Os, Ir --.

In Column 3, Lines 9-10, delete "pentamethylcyclopendienyltrimethoxy" and insert
-- pentamethylcyclopentadienyltrimethoxy --.

In Column 3, Line 10, delete "ethylcycopentadienyl" and insert -- ethylcyclopentadienyl --.

In Column 3, Line 16, delete "tertbuylamino" and insert -- tertbutylamino --.

In Column 3, Line 17, delete "bistertbuylamino" and insert -- bistertbutylamino --.

In Column 4, Line 48, delete "cylopentadien" and insert -- cyclopentadien --.

In Column 4, Line 50, delete "anthrancenyl" and insert -- anthracenyl --.

Signed and Sealed this
Twenty-third Day of June, 2020

Andrei Iancu
*Director of the United States Patent and Trademark Office*

CERTIFICATE OF CORRECTION (continued)
U.S. Pat. No. 10,570,514 B2

In Column 4, Line 67, delete "siliyl" and insert -- silyl --.

In Column 11, Line 3, delete "(Vb)" and insert -- (Vb). --.

In Column 16, Line 32, delete "then" and insert -- than --.

In the Claims

In Column 17, Line 24 (approx.), Claim 1, delete "(Vb);" and insert -- (Vb): --.